(12) United States Patent
Wen et al.

(10) Patent No.: US 12,029,919 B2
(45) Date of Patent: Jul. 9, 2024

(54) DYNAMIC INTENSITY-MODULATED SEGMENTATION METHOD FOR ORTHOGONAL DOUBLE-LAYER GRATING DEVICE

(71) Applicant: SUZHOU LINATECH MEDICAL SCIENCE AND TECHNOLOGY, Jiangsu (CN)

(72) Inventors: Hu Er Wen, Jiangsu (CN); Jonathan Yi Yao, Jiangsu (CN)

(73) Assignee: SUZHOU LINATECH MEDICAL SCIENCE AND TECHNOLOGY CO., LTD., Jiangsu (CN)

( * ) Notice: Subject to any disclaimer, the term of this patent is extended or adjusted under 35 U.S.C. 154(b) by 569 days.

(21) Appl. No.: 17/417,085

(22) PCT Filed: Nov. 25, 2019

(86) PCT No.: PCT/CN2019/120600
§ 371 (c)(1),
(2) Date: Jun. 21, 2021

(87) PCT Pub. No.: WO2020/125332
PCT Pub. Date: Jun. 25, 2020

(65) Prior Publication Data
US 2022/0047893 A1 Feb. 17, 2022

(30) Foreign Application Priority Data

Dec. 21, 2018 (CN) .......................... 201811579085.8

(51) Int. Cl.
*A61N 5/10* (2006.01)
*G21K 1/06* (2006.01)

(52) U.S. Cl.
CPC ......... *A61N 5/1045* (2013.01); *A61N 5/1031* (2013.01); *G21K 1/067* (2013.01)

(58) Field of Classification Search
None
See application file for complete search history.

(56) References Cited

U.S. PATENT DOCUMENTS

| | | | |
|---|---|---|---|
| 2009/0080619 A1* | 3/2009 | Hasegawa | G21K 1/04 378/151 |
| 2013/0284951 A1* | 10/2013 | Echner | G21K 1/046 250/505.1 |

(Continued)

FOREIGN PATENT DOCUMENTS

| | | |
|---|---|---|
| CN | 101246757 A | 8/2008 |
| CN | 102915784 A | 2/2013 |

(Continued)

*Primary Examiner* — Hoon K Song
(74) *Attorney, Agent, or Firm* — Muncy, Geissler, Olds & Lowe, P.C.

(57) ABSTRACT

The invention discloses a dynamic intensity-modulated segmentation method for an orthogonal double-layer grating blade device. The core of the segmentation algorithm is to construct a virtual single-layer grating after the velocities of the two-layer gratings are synthesized to perform dynamic intensity modulation of the single-layer grating (sliding-window) segmentation, and finally use two layers of gratings to conform to each segment. In order to reduce the segmentation error, the invention provides two optimization methods: blade motion trajectory optimization method and segment weight optimization method. The blade motion trajectory optimization method is to optimize the objective function under certain constraints with the motion trajectory of each blade as a variable under the condition that the segment weight is fixed. Segment weight optimization method is to optimize the time points of each segment when the blade motion trajectory is fixed. Both of the two optimization methods can reduce the error of the segmentation intensity and improve the optimization effect.

7 Claims, 8 Drawing Sheets

(56) References Cited

U.S. PATENT DOCUMENTS

2017/0232274 A1* 8/2017 Isola .................... A61N 5/1045
                                                          600/1
2018/0043187 A1* 2/2018 Yao ..................... A61B 6/4035

FOREIGN PATENT DOCUMENTS

| CN | 103079643 A | 5/2013 |
|---|---|---|
| CN | 107349531 A | 11/2017 |
| CN | 108066902 A | 5/2018 |
| CN | 108211136 A | 6/2018 |
| CN | 109499011 A | 3/2019 |
| KR | 20150008706 A | 1/2015 |

* cited by examiner (a)          (b)

(a)          (b)

(a)          (b)

(a)          (b)          (c)

DYNAMIC INTENSITY-MODULATED SEGMENTATION METHOD FOR ORTHOGONAL DOUBLE-LAYER GRATING DEVICE

TECHNICAL FIELD

The invention relates to the field of medical technology, and mainly relates to a segmentation method (sliding window) for an orthogonal double-layer grating device of inverse intensity modulated radiotherapy.

TECHNICAL BACKGROUND

At present, the most common technique in radiotherapy is to use grating blade for intensity modulation. Through the grating blades' movement, the target area can have a very good conformal effect, and can reduce the radiation damage of normal tissue. In general, for the grating blades, the thinner and greater number of the grating blades, the better the conformal degree of the multi-lobed collimator. But for conventional single-layer grating blade, because blades can only move in one direction, the blade thickness direction of the conformal ability is limited, for parallel double-layer multi-layer collimator, although the blade thickness direction compared with the single-layer grating conformal ability improved, however, due to the influence of the thickness of the leaf, it cannot move or form a radiation unit at any position.

In contrast, orthogonal double-layer gratings (as shown in FIG. 1 and FIG. 2) have several advantages:
1) Better conformity of the blade in the thickness direction;
2) High irradiating efficiency for complex fields;
3) It can effectively reduce the leakage of the grating, and can better protect the organs at risk.

Dynamically intensity-modulated segmentation realizes the segmentation of intensity map by simultaneously controlling the velocity and dose rate of each pair of blades. In dynamic segmentation, if the blades can be overlapped, the segmentation algorithms of each pair of blades are calculated independently without interference. Compared with static segmentation, dynamic segmentation has obvious advantages of high irradiation efficiency and steep dose curve in target area. However, dynamic segmentation requires more MU to complete, and the control system is more complex.

The dynamic segmentation of orthogonal double-layer gratings theoretically has high illumination efficiency, and has the advantages of orthogonal double-layer gratings and dynamic segmentation, but its disadvantage is that when doing dynamic segmentation, the segmentation algorithm of each pair of blades is no longer independent. The blade motions in the two directions are coupled with each other and affect the segmentation intensity map at the same time, which greatly increases the difficulty of the algorithm Its implementation has not yet been reported in the papers or published by major radiotherapy companies, in other words, this area of research has not been studied.

Therefore, a dynamic sliding-window subfield segmentation method suitable for orthogonal double-layer grating device needs to be proposed, which can fill the gap in this field and provide reference for the subsequent research.

The Invention Contents

In order to solve the above technical problems, the present invention presents a dynamic intensity-modulated segmentation method (sliding-window) for the orthogonal double-layer grating device.

In order to achieve the above purpose, the technical scheme of the invention is as follows: The dynamic intensity-modulated segmentation method for the orthogonal double-layer grating device includes the following steps:

S1: construct a virtual single-layer grating, the velocity of the virtual single-layer grating is composed of the velocity of the orthogonal double-layer grating, and set the blade thickness and blade logarithm of the virtual single-layer grating;

S2: obtain the optimization intensity map, and then rotate the optimization intensity map according to the installation angle of the virtual single-layer grating obtained in Step S S3: the dynamic intensity modulation calculation is carried out for the rotated optimization intensity map obtained in Step S2, and the calculation results include the time point of the inflection point of velocity and the shapes of each segment, the preliminary calculated intensity map can be obtained by stacking each segment shape, and the comparison with the optimization intensity map can be used to check whether the segment formed by the virtual single-layer grating meets the expectation.

S4: the real segment is obtained by inverse rotation of the segment formed by the virtual single-layer grating;

S5: the orthogonal double-layer grating is used to conformal the anti-rotated segments obtained in step S4;

S6: check whether the blades of the orthogonal double-layer grating are overspeed, if overspeed, limit the overspeed blades and allow the blades to retreat.

On the basis of the above technical solution, the following improvements may also be made:

As a preferred solution, in step S1, the velocity of the virtual single-layer grating device is the velocity synthesis of the orthogonal grating A and grating B, and the magnitude and direction of the velocity are v, θ;

$$v = \sqrt{v_1^2 + v_2^2} \quad (1)$$

$$\theta = \tan^{-1}\left(\frac{v_2}{v_1}\right) \quad (2)$$

Wherein, $v_1$ is the maximum velocity of the horizontal blade, and $v_2$ is the maximum velocity of the vertical blade, the blade thickness of the virtual single-layer grating is set as a smaller value, and the blade logarithm is set as a larger value, the other attributes are consistent with grating A or grating B.

As a preferred solution, step S2 also includes the following content, when the optimization intensity map is rotated according to the installation angle of the virtual single-layer grating obtained in step S1, the sampling interval of the optimization intensity map in the direction of the blade thickness is directly divided according to the blade thickness, and the sampling interval in the direction of the blade movement is divided according to the interval of customized, with a value of 0.25.

As a preferred solution, step S3 specifically includes the following steps:

S3.1: calculate the minimum increment of flux;
in order to ensure that the blade will not be closed during movement, the minimum distance (Gap) between blade pairs is known, so the minimum increment of unit length needs to be calculated, as shown in Equation (3), when the blade runs unit length at the maximum physical speed, the flux per unit length is the minimum, and the product of min slope and Gap is the minimum intensity value that the blade can reach;

$$\min \text{ slope} = \frac{DoseRatio}{MaxDose \times MaxSpeed} \quad (3)$$

S3.2: calculate the relationship between flux and distance, according to the optimization intensity map after rotation of step S2 and the minimum increment of flux to determine the corresponding curve of intensity flux and position during the movement of left and right blades;

S3.3 set the inflection point of velocity, the inflection point of velocity is calculated according to the relationship curve between flux and distance;

S3.4: determine the position of the left and right blades in segments, taking the inflection point of velocity as the segmentation point, calculate the positions of the left and right blades at each segmentation point;

S3.5: check the blade acceleration, if the maximum acceleration of the blade exceeds the limit, reduce the maximum velocity of the grating and repeat steps S3.1-S3.4;

S3.6: contrast the intensity map, calculate the intensity map under the current segmentation and compare it with the optimization intensity map, when the error is greater than the threshold, adjust the intensity map under the current segmentation and repeat steps S3.1-S3.5.

As a preferred solution, it also includes the optimization of the dynamic intensity-modulated field segmentation method for the orthogonal double-layer grating, specifically the segment weight optimization method:

the segment weight optimization method is to optimize the time point of each segment under the condition of a fixed blade trajectory, and the optimization objective is the two norms of the difference between the segmentation intensity map and the optimization intensity map, as shown in Equation (4);

$$J_{obj} = \|J_{opt} - J_{cal}\|_2 \quad (4)$$

the segmentation intensity map can be regarded as the linear superposition of each segment, as shown in Equation (5);

$$I_{cal} = \sum_u u_i I_{seg} \quad (5)$$

wherein, $I_{seg}$ is the intensity map formed by a single segment, $u_i$ is the weight of the segment, and the objective function is $J_{obj}$.

As a preferred solution, it also includes the optimization of the dynamic intensity-modulated segmentation method for the orthogonal double-layer grating, specifically the blade motion trajectory optimization method;

the blade motion trajectory optimization method of the blade motion trajectory is to optimize the objective function under certain conditions by taking the motion trajectory of each blade as a variable under the condition that the weight of the segment is fixed.

As a preferred solution, the blade motion trajectory optimization method specifically includes the following steps:

S7: calculate the intensity map formed by the superposition of the current blade position; the motion trajectory of each pair of blades of horizontal grating is denoted as:

$$X = \{x_{ly_1}(t), x_{ry_1}(t), x_{ly_2}(t), x_{ry_2}(t), \ldots, x_{ly_n}(t), x_{ry_n}(t)\} \quad (6)$$

the motion trajectory of each pair of blades of the vertical grating is denoted as:

$$Y = \{y_{dx_1}(t), y_{ux_1}(t), y_{dx_2}(t), y_{ux_2}(t), \ldots, y_{dx_m}(t), y_{ux_m}(t)\} \quad (7)$$

wherein, $x_{ly_i}(t)$ represents the motion trajectory of the left blade of the i-th pair of blades (the corresponding Y-axis coordinate is $y_i$); $x_{ry_i}(t)$ represents the motion trajectory of the right blade of the i-th pair of blades (the corresponding Y-axis coordinate is $y_i$); $y_{dx_j}(t)$ represents the motion trajectory of the lower blade of the j-th pair of blades (the corresponding Y-axis coordinate is $x_j$); $y_{ux_j}(t)$ represents the motion trajectory of the upper blade of the j-th pair of blades (the corresponding Y-axis coordinate is $x_j$); there are n pairs of horizontal blades and m pairs of vertical blades;

blade movement is subject to the following constraints: jaw constraint, blade physical constraint and velocity constraint, the constraint conditions are shown in Equation (8):

$$\begin{cases} x_{min} \leq x_{ly_i}(t) \leq x_{ry_i}(t) \leq x_{max} \\ y_{min} \leq y_{dx_j}(t) \leq y_{ux_j}(t) \leq y_{max} \\ -v_{1max} \leq \frac{dx_{ly_i}(t)}{dt} \leq v_{1max}, -v_{1max} \leq \frac{dx_{ry_i}(t)}{dt} \leq v_{1max} \\ -v_{2max} \leq \frac{dy_{dx_j}(t)}{dt} \leq v_{2max}, -v_{2max} \leq \frac{dy_{ux_j}(t)}{dt} \leq v_{2max} \end{cases} \quad (8)$$

then, the calculated intensity map obtained from the above blade trajectory is:

$$I(x, y) = \int_0^T H(x - x_{ly_i}(t)) \cdot H(x_{ry_i}(t) - x) \cdot H(y - y_{dx_j}(t)) \cdot H(y_{ux_j}(t) - y) \quad (9)$$

$$H(x) = \begin{cases} 1, x \geq 0 \\ 0, x < 0 \end{cases} \quad (10)$$

wherein, i and j are the blade serial numbers of horizontal grating and vertical grating corresponding to the point (x,y); the segmentation intensity map can be regarded as the linear superposition of each segment, as shown in Equation (5);

$$I_{cal} = \sum_u u_i I_{seg} \quad (11)$$

wherein, $I_{seg}$ is the intensity map formed by a single segment, $u_i$ is the segment weight; the objective function is $J_{obj}$, and the optimization objective function is the two forms of the difference between the segmented intensity map and the optimization intensity map, as shown in Equation (4);

$$J_{obj} = \|J_{opt} - J_{cal}\|_2 \quad (12)$$

S8: begin the outer loop to find the rows and columns that differ most from the segmentation intensity map and the optimization intensity map, the evaluation criterion of difference value is two norms;

S9: find the blade sequence number corresponding to the row and column with the greatest difference, there is a fixed correspondence relationship between grating and intensity map, the blade sequence number can be calculated according to the intensity map number;

S10: start the internal cycle, select a moment at random, calculate the activity range of the four blades on the upper, lower, left and right sides according to the constraint conditions, and the calculation method is shown in Equation (8);

S11: the position of the upper, lower, left and right blades is changed in a cycle, according to step S10, the four blades are given a range of activity, the maximum and minimum values of the range of the four blades are taken in a cycle to perturb the positions of the four blades respectively;

S12: if the objective function has a decline or the internal cycle exceeds the limit, step S13 will be entered; otherwise, step S10-S11 will be repeated;

S13: if the objective function is less than the threshold value or the external cycle exceeds the limit, the optimization will be stopped, otherwise, steps S8-S12 will be repeated.

BRIEF DESCRIPTION OF THE DRAWINGS

FIG. 5 (a) is a first optimization intensity map provided by embodiments of the invention;

FIG. 5 (b) is a first optimization intensity map after rotation corresponding to FIG. 5 (a);

FIG. 6 (a) is a second optimization intensity map provided by embodiments of the invention;

FIG. 6 (b) is a second optimization intensity map after rotation corresponding to FIG. 6 (a);

FIG. 7 (a) is a first optimization intensity map after rotation provided by embodiments of the invention;

FIG. 7 (b) is the superposition map of segment corresponding to FIG. 7 (a);

FIG. 12 (a) is a third optimization intensity map provided by embodiments of the invention;

FIG. 12 (b) is the segmentation intensity map corresponding to FIG. 12 (a);

FIG. 12 (c) is the optimized intensity map corresponding to FIG. 12 (a).

DETAILED DESCRIPTION OF THE EMBODIMENTS

The preferred mode of implementation of the invention is described in detail in combination with the attached figures below.

To achieve the purpose of the present invention, a dynamic intensity-modulated segmentation method for an orthogonal double-layer grating is proposed. The method is based on an orthogonal double-layer grating for radiotherapy equipment, which is installed under the accelerator head, and comprises:

The plane of the upper grating blade and the lower grating blade is parallel to each other and perpendicular to the direction of the ray emitted by the accelerator head. The motion direction of the upper grating blade and the lower grating blade is orthogonal.

The upper grating blade includes a left blade and a right blade, which is used to search and move to the left and right sides of the target area.

The lower grating blade includes an upper blade and a lower blade, which is used to search and move to the upper and lower sides of the target area.

The controller is used to drive each sub-blade in the left blade and the right blade, upper blade and lower blade to move separately in order to achieve the purpose of conformal with the target area.

Compared with the traditional single-layer grating and the double-layer parallel grating, the orthogonal double-layer grating has higher conformity, and the positioning accuracy are less than 1 mm for both directions.

Figure 1:
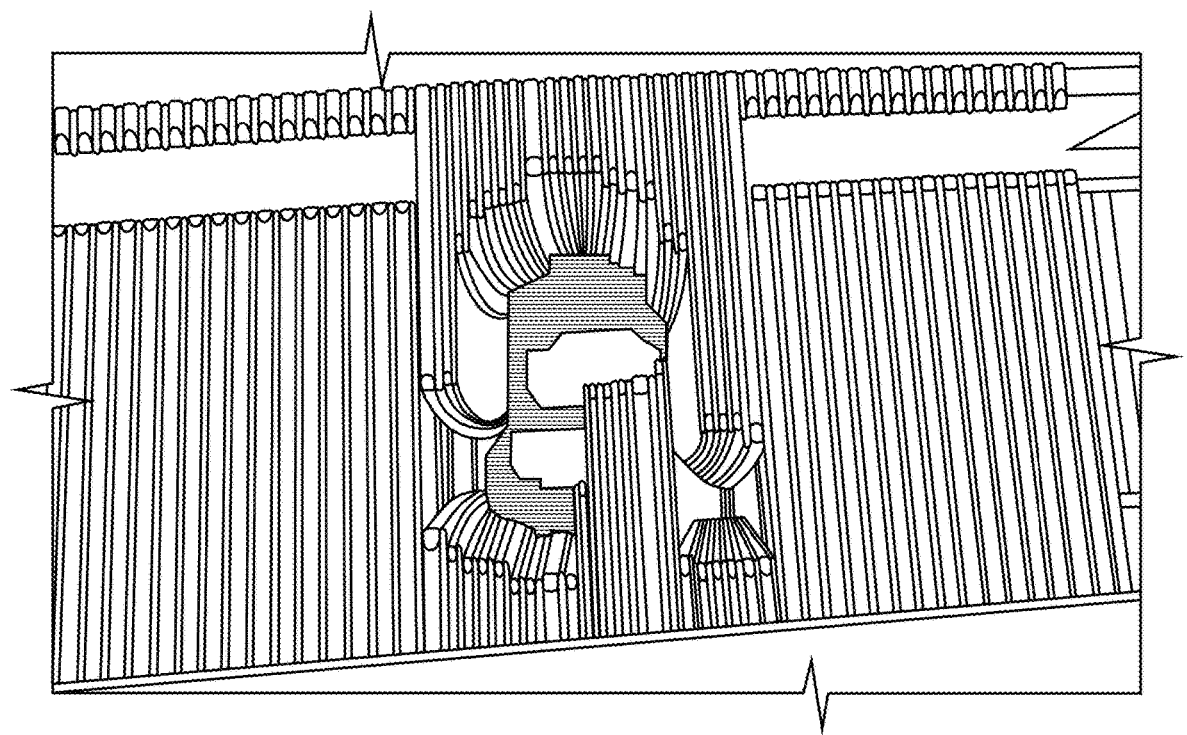
FIG. 1 is a first instance diagram of solving segmentation in a multiconnected region with orthogonal double-layer grating.
Figure 2:
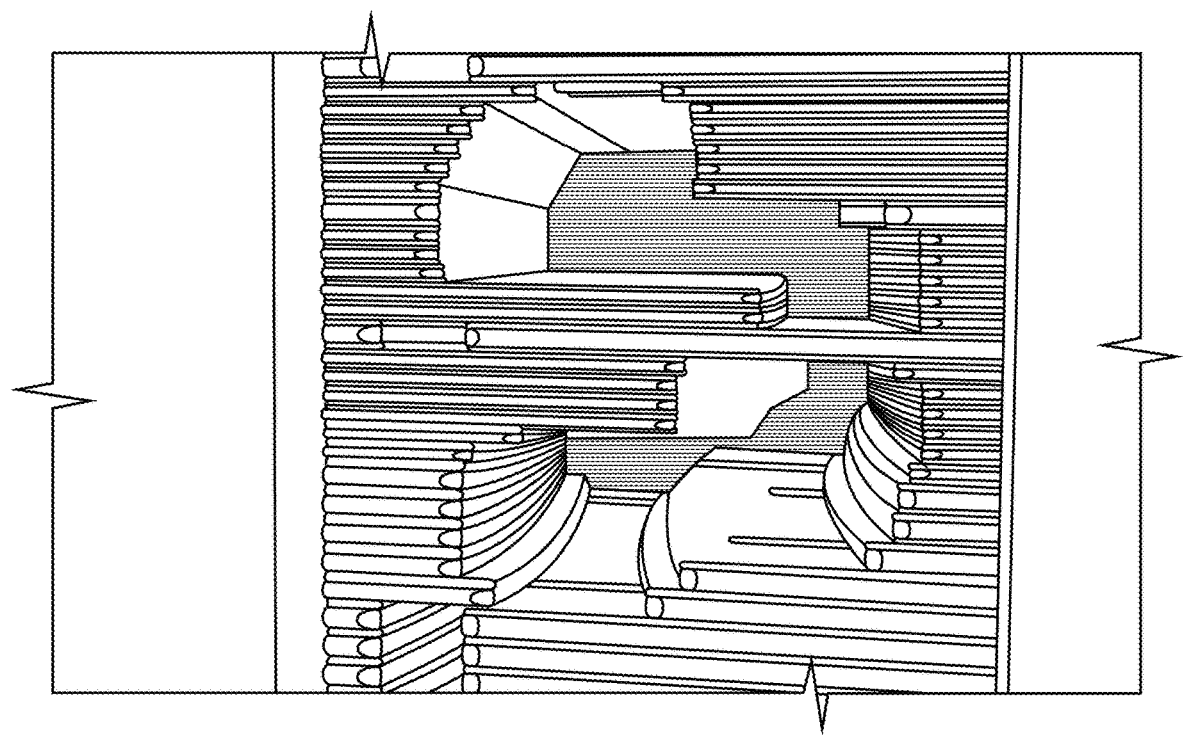
FIG. 2 is a second instance diagram of solving segmentation in a multiconnected region with orthogonal double-layer grating blade.
Figure 3:
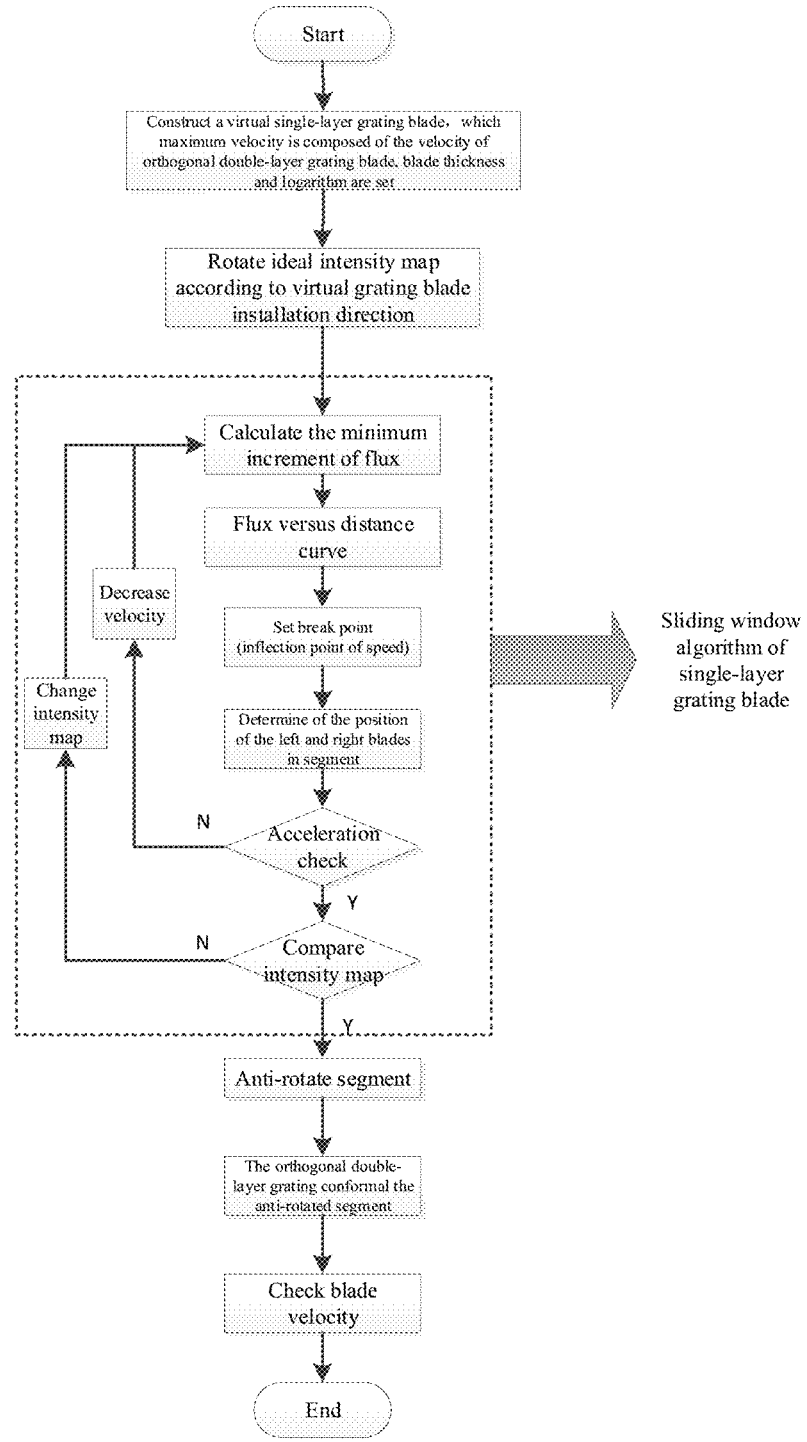
FIG. 3 is an overall flow chart of a dynamic intensity-modulated segmentation method for an orthogonal double-layer grating.

The invention is described in detail below, in some of the examples of a dynamically intensity-modulated segmentation method for an orthogonal double-layer grating blade, the following steps are included, as shown in FIG. 3:

S1: Construct a virtual single-layer grating, the velocity of the virtual single-layer grating is composed of the velocity of the orthogonal double-layer grating blade, and set the blade thickness and blade logarithm of the virtual single-layer grating.

S2: Obtain the optimization intensity map, and then rotate the optimization intensity map according to the installation angle of the virtual single-layer grating obtained in Step S1.

S3: The dynamic intensity modulation calculation is carried out for the rotated optimization intensity map obtained in Step S2, and the calculation results include the time point of the inflection point of velocity and the shapes of each segment. The preliminary calculated intensity map can be obtained by stacking each segment shape, and the comparison with the optimization intensity map can be used to check whether the segment formed by the virtual single-layer grating meets the expectation.

S4: The real segment is obtained by inverse rotation of the segment formed by the virtual single-layer grating.

S5: Orthogonal double-layer grating blade is used to conformal the anti-rotated segments obtained in step S4.

S6: Check whether the blades of the orthogonal double-layer grating are overspeed. If overspeed, limit the overspeed blades and allow the blades to retreat.

Wherein, step S3 is the segmentation step of the dynamic intensity-modulated of the virtual single-layer grating. After the segmentation is completed, step S4 obtains the segment shapes at each inflection point of velocity, and step S4 rotates the segment shapes inversely θ. In step S5, the orthogonal double-layer grating is conformal to the segment after inverse rotation obtained in step S4. Here, the segment formed by the virtual single-layer grating is realized by the orthogonal double-layer grating, and the motion curve of the orthogonal double-layer grating at each velocity inflection point is obtained.

In order to further optimize the implementation effect of the present invention, in some other embodiments, the remaining characteristic techniques are the same. The difference is that, in step S1, the velocity of the virtual single-layer grating is the velocity synthesis of the orthogonal grating A (MLC1) and grating B (MLC2), the magnitude and direction of the velocity are v, θ;

$$v = \sqrt{v_1^2 + v_2^2} \tag{1}$$

$$\theta = \tan^{-1}\left(\frac{v_2}{v_1}\right) \tag{2}$$

Wherein, $v_1$ is the maximum velocity of the horizontal blade, and $v_2$ is the maximum velocity of the vertical blade. The blade thickness of the virtual single-layer grating is set as a small value (0.25 or other here), and the blade logarithm is set as a large value (256 or other here). The remaining attributes are consistent with grating A or grating B.

Further, the following contents are included in Step S2. After the optimization intensity map is rotated in accordance with the installation angle θ of the virtual single-layer grating obtained in Step S1, the sampling interval of the optimization intensity map in the direction of blade thickness is directly divided according to the blade thickness, while in the direction of blade movement, the sampling interval is divided according to the custom interval, with a value of 0.25. Further, step S3 specifically includes the following steps;

S3.1: Calculate the minimum increment of flux.

In order to ensure that the blade will not be closed during movement, the minimum distance (Gap) between blade pairs is known, so the minimum increment of unit length needs to be calculated. As shown in Equation (3), when the blade runs unit length at the maximum physical speed, the flux per unit length is the minimum, and the product of min slope and Gap is the minimum intensity value that the blade can reach.

$$\min \text{ slope} = \frac{DoseRatio}{MaxDose \times MaxSpeed} \tag{3}$$

S3.2: Calculate the relationship between flux and distance, according to the optimization intensity map after rotation of step S2 and the minimum increment of flux to determine the corresponding curve of intensity flux and position during the movement of left and right blades.

S3.3 Set the inflection point of velocity, the inflection point of velocity is calculated according to the relationship curve between flux and distance.

S3.4: Determine the position of the left and right blades in segments, taking the inflection point of velocity as the segmentation point, calculate the positions of the left and right blades at each segmentation point.

S3.5: Check the blade acceleration, if the maximum acceleration of the blade exceeds the limit, reduce the maximum velocity of the grating and repeat steps S3.1-S3.4.

S3.6: Contrast the intensity map, calculate the intensity map under the current segmentation and compare it with the optimization intensity map. When the error is greater than the threshold, adjust the intensity map under the current segmentation and repeat steps S3.1-S3.5.

In order to further optimize the implementation effect of the present invention, the remaining feature techniques are the same in other implementation methods, but the difference is that it also includes the optimization of the orthogonal double-layer grating dynamic intensity-modulated segmentation method, which is the segment weight optimization method.

Segment weight optimization method is to optimize the time point of each segment under the condition of a fixed blade trajectory, and the optimization objective is the two norms of the difference between the segmentation intensity map and the optimization intensity map, as shown in Equation (4).

$$J_{obj} = \|J_{opt} - J_{cal}\|_2 \tag{4}$$

The segmentation intensity map can be regarded as the linear superposition of each segment, as shown in Equation (5).

$$I_{cal} = \sum_u u_i I_{seg} \tag{5}$$

Wherein, $I_{seg}$ is the intensity map formed by a single segment, $u_i$ is the weight of the segment, and the objective function is $J_{obj}$.

Therefore, the segment weight optimization method is a quadratic programming problem with constraints, which can be solved according to the general solution idea.

In order to further optimize the implementation effect of the present invention, in some other implementation methods, the remaining feature technologies are the same, the difference is that it also includes the optimization of the orthogonal double-layer grating blade dynamic intensity-modulated segmentation method, which is the blade motion trajectory optimization method;

The blade motion trajectory optimization method takes the trajectory of each blade as a variable and optimizes the objective function under certain conditions under the condition that the weight of segment is fixed.

The blade motion is discretized, and the MU step (time point of inflection point of velocity) calculated by the virtual single-layer grating is the time interval. After discretization of the leaf, the trajectory of the blade can be represented by a series of points. According to the preliminary statistics, the number of trajectory points of all blades is about 20,000, that is to say, the optimization variables are about 20,000. The ordinary optimization methods, such as nonlinear optimization, genetic algorithm and particle swarm optimization algorithm, their effects are not significant. Therefore, an optimization algorithm is provided here. The whole optimization process is divided into outer loop and internal loop. The outer loop looks for the row and column with the greatest difference between the segmentation intensity map and the optimization intensity map, and calculates the corresponding blade sequence number. The purpose of this step is to lock the blade sequence number to be optimized and reduce the number of variables to be optimized. If the number of iterations of the outer loop exceeds the limit or the objective function meets the requirements, the whole loop will be quit. The internal loop randomly selects the moment of the blade, calculates the range of motion of the blade according to the constraint conditions, changes between the maximum and minimum value of the range of motion of the blade, and observes whether the objective function becomes smaller. If the objective function drops or the number of iterations of the internal loop is excessive, break out of the internal loop.

Figure 4:
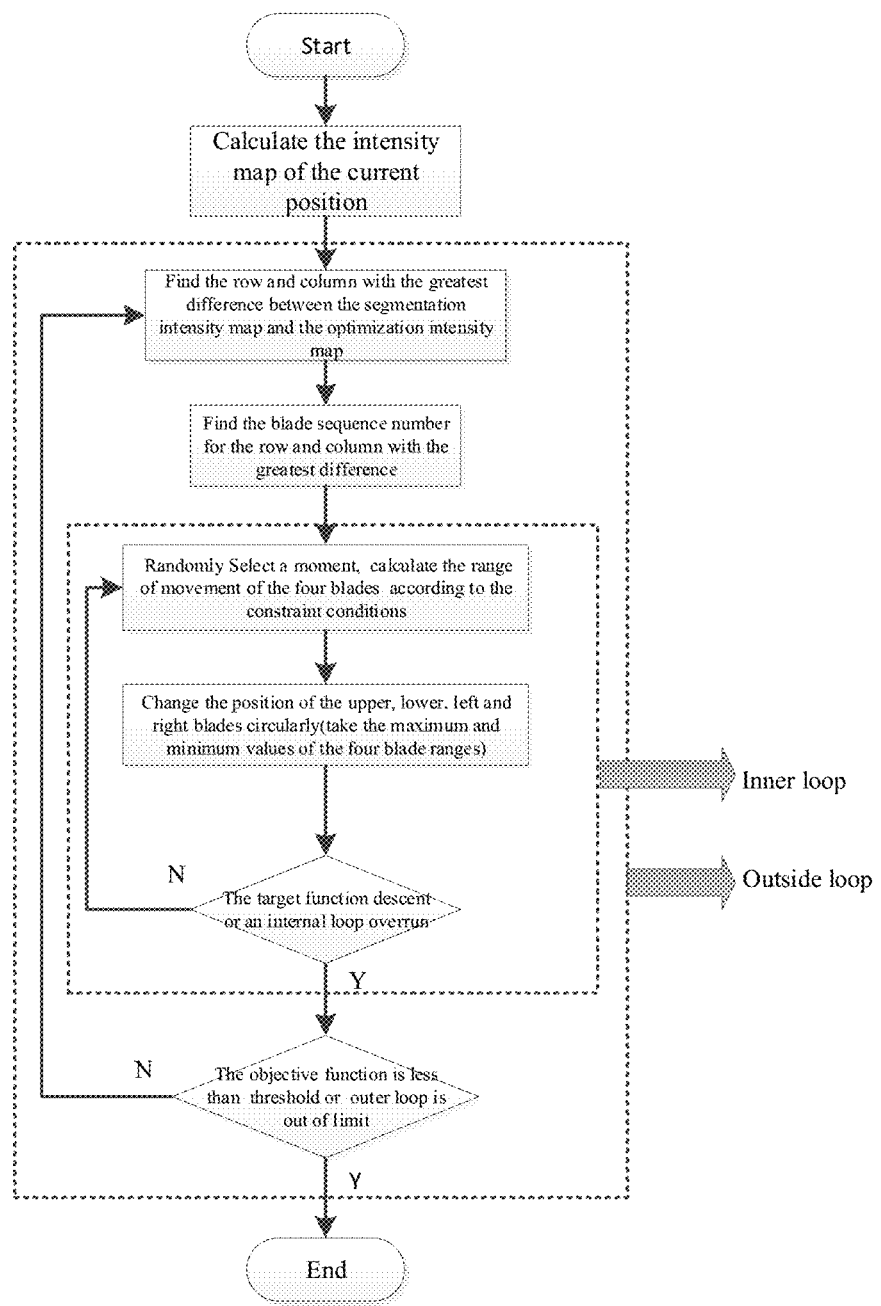
FIG. 4 is the flow chart of the blade motion trajectory optimization method.

Further, the blade motion trajectory optimization method includes the following steps, as shown in FIG. 4:

S7: calculate the intensity map formed by the superposition of the current blade position; the motion trajectory of each pair of blades of horizontal grating is denoted as:

$$X=\{x_{ly_1}(t), x_{ry_1}(t), x_{ly_2}(t), x_{ry_2}(t), \ldots, x_{ly_n}(t), x_{ry_n}(t)\} \quad (6)$$

the motion trajectory of each pair of blades of the vertical grating is denoted as:

$$Y=\{y_{dx_1}(t), y_{ux_1}(t), y_{dx_2}(t), y_{ux_2}(t), \ldots, y_{dx_m}(t), y_{ux_m}(t)\} \quad (7)$$

wherein, $x_{ly_i}(t)$ represents the motion trajectory of the left blade of the i-th pair of blades (the corresponding Y-axis coordinate is $y_i$); $x_{ry_i}(t)$ represents the motion trajectory of the right blade of the i-th pair of blades (the corresponding Y-axis coordinate is $y_i$); $y_{dx_j}(t)$ represents the motion trajectory of the lower blade of the j-th pair of blades (the corresponding Y-axis coordinate is $x_j$); $y_{ux_j}(t)$ represents the motion trajectory of the upper blade of the j-th pair of blades (the corresponding Y-axis coordinate is $x_j$); there are n pairs of horizontal blades and m pairs of vertical blades;

blade movement is subject to the following constraints: jaw constraint, blade physical constraint and velocity constraint, the constraint conditions are shown in Equation (8):

$$\begin{cases} x_{min} \le x_{ly_i}(t) \le x_{ry_i}(t) \le x_{max} \\ y_{min} \le y_{dx_j}(t) \le y_{ux_j}(t) \le y_{max} \\ -v_{1max} \le \dfrac{dx_{ly_i}(t)}{dt} \le v_{1max}, -v_{1max} \le \dfrac{dx_{ry_i}(t)}{dt} \le v_{1max} \\ -v_{2max} \le \dfrac{dy_{dx_j}(t)}{dt} \le v_{2max}, -v_{2max} \le \dfrac{dy_{ux_j}(t)}{dt} \le v_{2max} \end{cases} \quad (8)$$

then, the calculated intensity map obtained from the above blade trajectory is:

$$I(x, y) = \int_0^T H(x - x_{ly_i}(t)) \cdot H(x_{ry_i}(t) - x) \cdot H(y - y_{dx_j}(t)) \cdot H(y_{ux_j}(t) - y) \quad (9)$$

$$H(x) = \begin{cases} 1, x \ge 0 \\ 0, x < 0 \end{cases} \quad (10)$$

wherein, i and j are the blade serial numbers of horizontal grating and vertical grating corresponding to the point (x, y); the segmentation intensity map can be regarded as the linear superposition of each segment, as shown in Equation (5);

$$I_{cal} = \sum_u u_i I_{seg} \quad (11)$$

wherein, $I_{seg}$ is the intensity map formed by a single segment, is the segment weight; the objective function is $J_{obj}$, and the optimization objective function is the two forms of the difference between the segmented intensity map and the optimization intensity map, as shown in Equation (4);

$$J_{obj}=\|J_{opt}-J_{cal}\|_2 \quad (12)$$

S8: begin the outer loop to find the rows and columns that differ most from the segmentation intensity map and the optimization intensity map, the evaluation criterion of difference value is two norms;

S9: find the blade sequence number corresponding to the row and column with the greatest difference, there is a fixed correspondence relationship between grating and intensity map, the blade sequence number can be calculated according to the intensity map number;

S10: start the internal cycle, select a moment at random, calculate the activity range of the four blades on the upper, lower, left and right sides according to the constraint conditions, and the calculation method is shown in Equation (8);

S11: the position of the upper, lower, left and right blades is changed in a cycle, according to step S10, the four blades are given a range of activity, the maximum and minimum values of the range of the four blades are taken in a cycle to perturb the positions of the four blades respectively;

S12: if the objective function has a decline or the internal cycle exceeds the limit, step S13 will be entered; otherwise, step S10-S11 will be repeated;

S13: if the objective function is less than the threshold value or the external cycle exceeds the limit, the optimization will be stopped, otherwise, steps S8-S12 will be repeated.

In summary, the present invention provides a dynamic intensity-modulated segmentation method for an orthogonal double-layer grating, and two methods for optimizing this segmentation are provided: blade motion trajectory optimization method and segment weight optimization method. Segment weight optimization method is to optimize the time points of each segment under the condition of fixed blade trajectory. Blade trajectory optimization method is to optimize the objective function under certain constraints by taking the trajectory of each blade as the variable under the condition of fixed blade trajectory weight.

In the existing segmentation technology, whether it is single-layer grating or parallel double-layer grating, will face two problems: the conformity in the blade thickness direction is not enough. A complex field needs many segments to form, so the irradiation efficiency is low. Orthogonal double-layer grating has advantages in both conformity and irradiation efficiency. In addition, double-layer grating can effectively reduce leakage and protect organs at risk (OARs) better. Compared with static segmentation, dynamic segmentation has obvious advantages of high irradiation efficiency and steep dose curve in target area.

Figure 5:
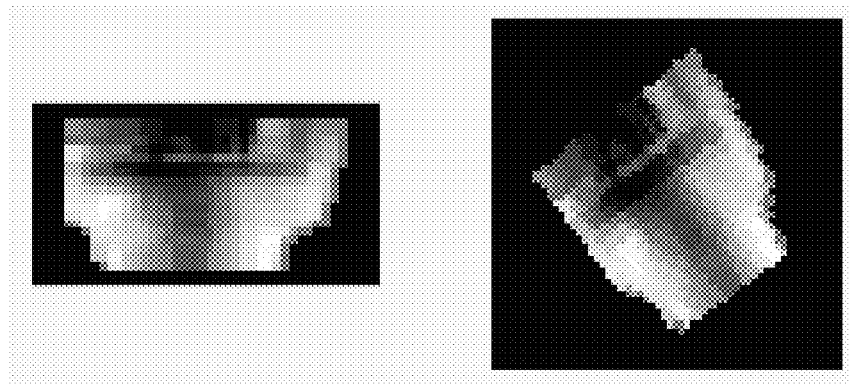
FIG. 5 is a first comparison diagram of the optimization intensity map and the rotated intensity map.
Figure 6:
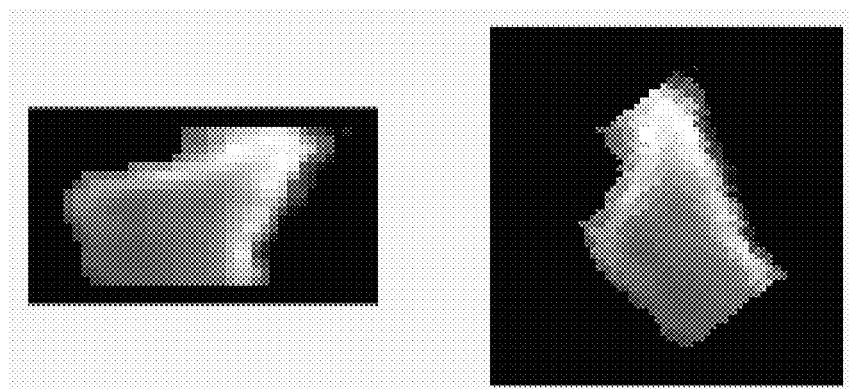
FIG. 6 is a second comparison diagram of the optimization intensity map and the rotated intensity map.

The invention starts by constructing a virtual single-layer grating blade, The grating blade installation direction is the velocity synthesis direction of the orthogonal double-layer grating blade. In order to facilitate the sliding-window segmentation of the virtual single-layer, the grating blade installation angle was rotated on the optimized intensity diagram obtained. The rotated map is still a rectangle, while the dimension expands, and the whole intensity map range becomes larger. The invention defines the sampling interval of the map after rotation by itself, which is not completely consistent with the sampling interval of the optimization intensity map. The optimization intensity map before and after rotation is shown in FIG. 5 and FIG. 6.

Figure 7:
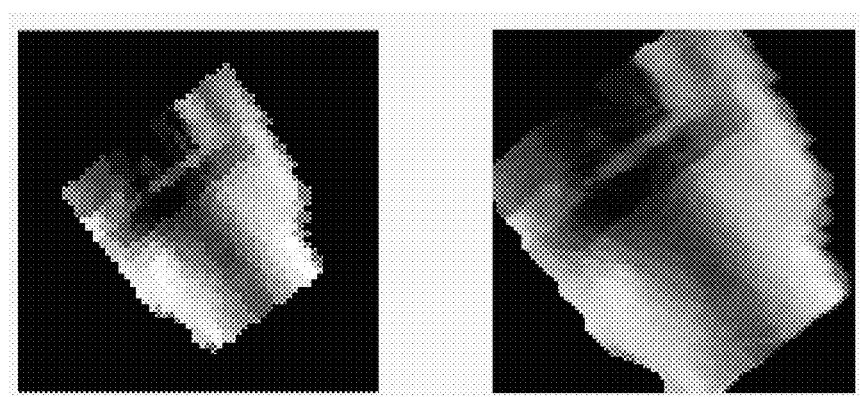
FIG. 7 is the comparison between the optimization intensity map after rotation provided by the embodiments of the invention and the superposition map of the segment.

Then the dynamic intensity-modulation calculation is carried out for the optimal intensity map after rotation. The calculation results include the time point of the velocity inflection point and shape of each segment. By stacking the shape of each segment, a preliminary computed intensity map can be obtained. Comparing with the optimization intensity map, it can be used to check whether the segment formed by the virtual grating meets the expectation. It can be seen from FIG. 7 that the segment formed by the virtual single-layer grating is reasonable.

Figure 8:
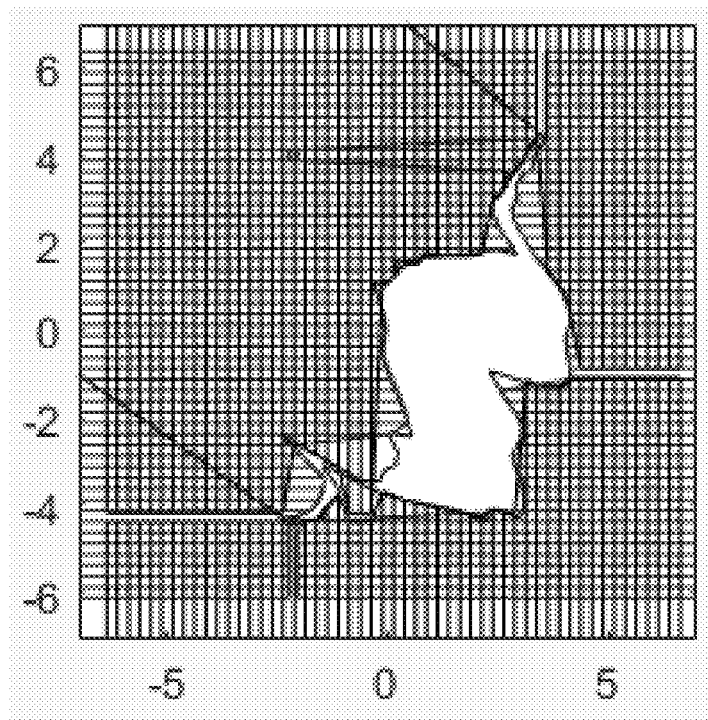
FIG. 8 is a first orthogonal double-layer grating segment conformal map provided by embodiments of the invention.
Figure 9:
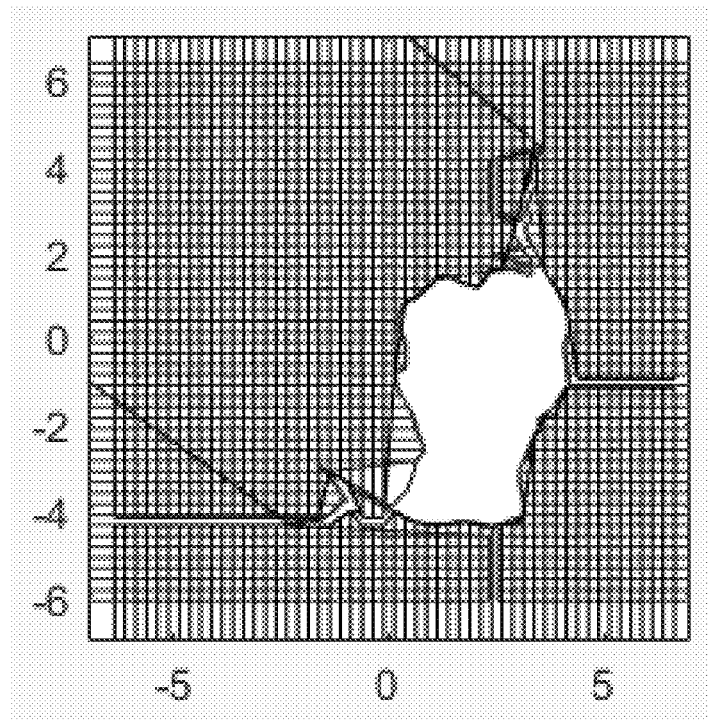
FIG. 9 is a second orthogonal double-layer grating segment conformal map provided by embodiments of the invention.

After the segment formed by the virtual single-layer grating is counter-rotated, the real segment is obtained. The existing orthogonal double-layer grating is used to conformal the counter-rotated segment, so as to obtain the calculation result of the sliding window of the orthogonal double-layer grating. Examples of conformal segment of orthogonal double-layer grating are shown in FIG. 8 and FIG. 9, where the blank area is the segment after anti-rotation, and the network form is the orthogonal double-layer grating, indicating that the orthogonal double-layer grating can correctly conformal the segment.

Figure 10:
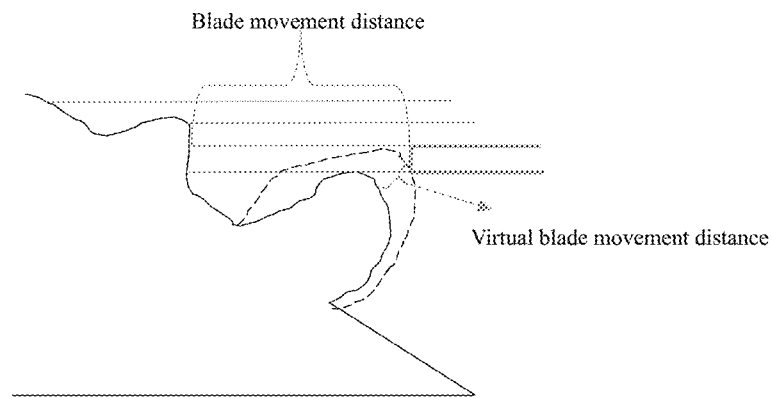
FIG. 10 shows the overspeed situation of the orthogonal double-layer grating blade.

Finally, check the blades for overspeed. The previous step has formed a segment shape at a series of time points, where the blade is checked for overspeed. It is worth noting that the problem of blade overspeed has been checked when the virtual single-layer grating forms the sliding-window segment. However, if the velocity-synthesized virtual single-layer grating does not overspeed, the orthogonal double-layer grating does not necessarily overspeed. As shown in FIG. 10, the moving distance of virtual blade is small, but the deviation of shape is large. When the horizontal grating is conformal, the moving distance increases sharply, causing blade overspeed and sometimes causing blade back. Therefore, the velocity check here differs from the sliding-window of a single-layer grating, allowing the blade to slide back.

In order to improve the existing sliding window segmentation of orthogonal double-layer grating, the invention proposes two optimization methods:

a) Blade motion trajectory optimization method, the blade position is taken as the variable, and the initial value is the blade position formed by the velocity synthesis algorithm. Constraint conditions were added, and the two-norm of the difference of the segment superposition strength map was taken as the objective for optimization.

b) Segment weight optimization method, the blade position is fixed at each moment, and the time at each moment is optimized (segment weight).

For the blade motion trajectory optimization method, the blade position should be initialized before the blade position optimization. The pseudocode of the variable arrangement rule here is:

For i=1: all times
  Arrange all left blades of the horizontal grating blade in sequence
  Arrange all right blades of the horizontal grating blade in sequence
  Arrange all the lower blades of the vertical grating blade in sequence
  Arrange all the upper blades of the vertical grating blade in sequence
end In this way, all the time of all the blades can be arranged in a row for easy maintenance;

Next, define the constraint function, constraint functions include jaw constraint, physical constraint and velocity constraint, the external data required are: jaw parameters, grating velocity, grating minimum spacing, the constraint function is shown in Equation (8). At the same time, the activity range of a blade at a certain time can be calculated according to this constraint function.

Define objective function. The intensity map needs to be calculated based on the existing blade position and time information. Discrete intensity maps formed by discrete blade positions will be transformed by actual positions. Therefore, external data required here are as follows: blade thickness and intensity map sampling interval, MU (time information).

Figure 11:
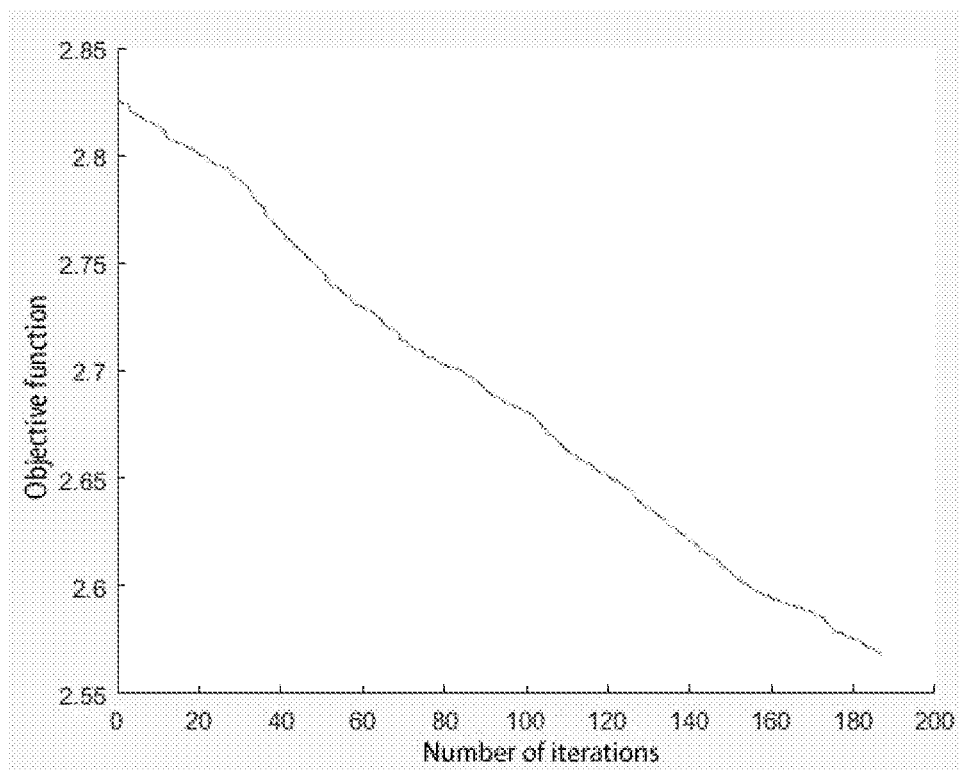
FIG. 11 shows the iterative curve of blade position optimization.

Finally, the blade position was optimized according to the steps shown in FIG. 4, and the curve between the number of iterations obtained and the objective function was shown in FIG. 11. It can be seen that in the iterative process, the objective function decreases slowly, and the optimized segmentation intensity map is closer to the optimization intensity map.

Figure 12:
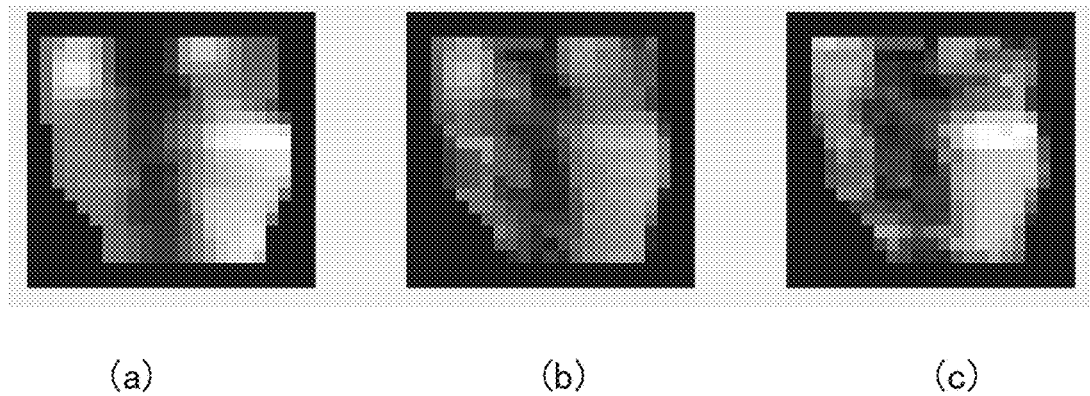
FIG. 12 is the comparison of the optimization intensity map, the segmented intensity map and the after optimized intensity map of the segment weight optimization method provided in the embodiment of the invention.
Figure 13:
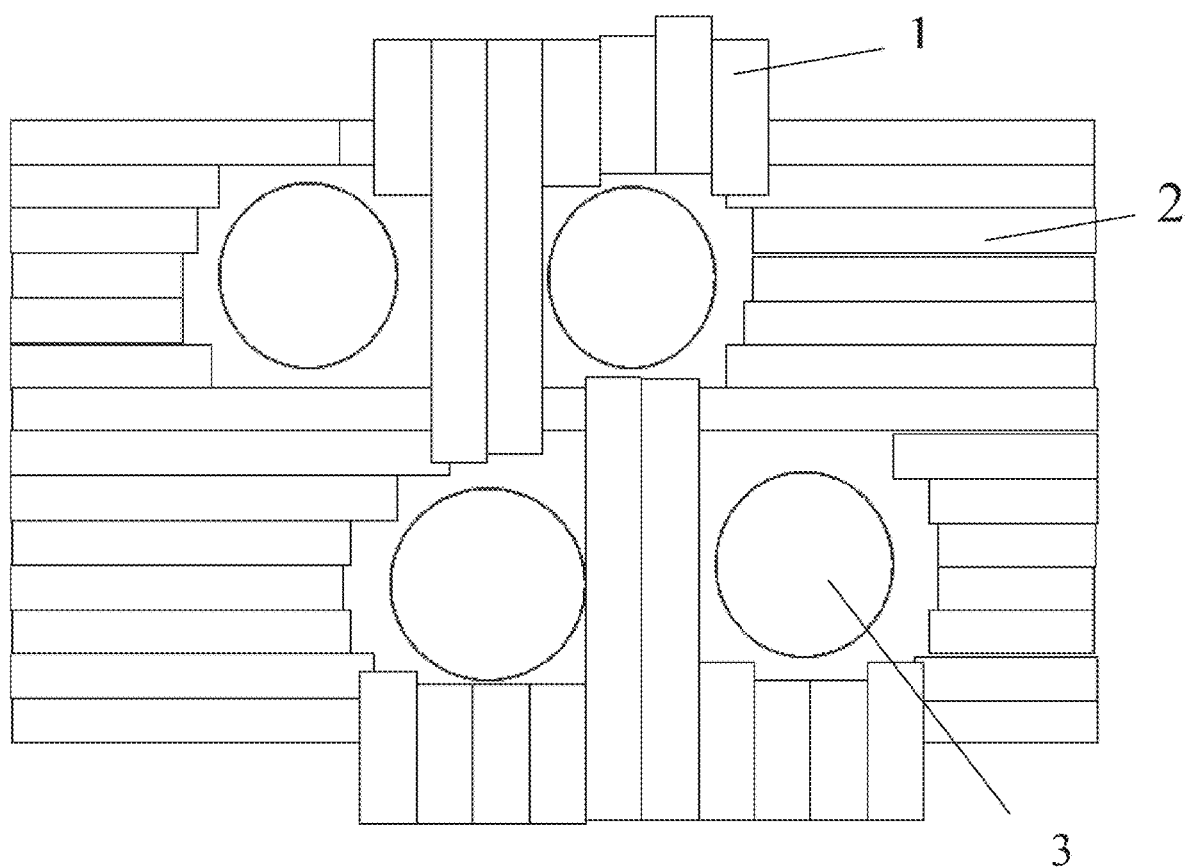
FIG. 13 is a schematic diagram of multiple emission fields segmented by the upper and lower two layers of grating.
Figure 14:
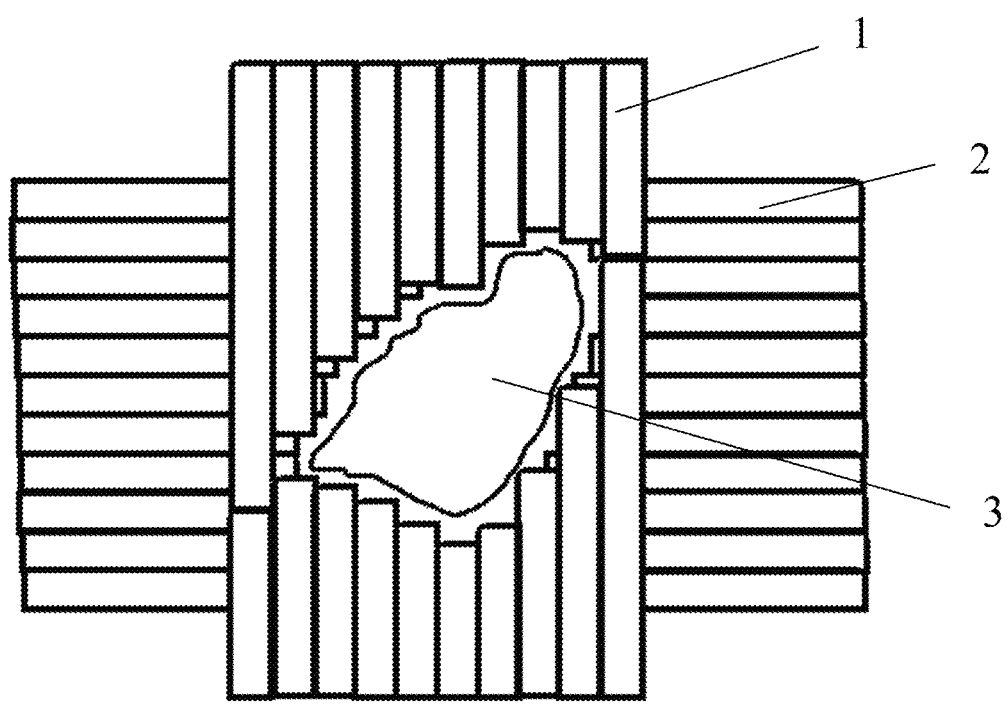
FIG. 14 is a schematic diagram of fitting optimization along the envelope of the radiation field edge with the combination of the upper and lower two layers of grating.

The segment weight optimization method is completed in one time and does not need repeated iteration. After optimization, the objective function is reduced from 2.8254 to 1.9457. The comparison of the optimization intensity map, the segmented intensity map and the after optimized intensity map is shown in FIG. 12, which shows that the optimization effect is obvious.

Orthogonal double-layer grating has obvious advantages in target conformal and therapy efficiency, the invention provides a dynamic intensity-modulated segmentation method for an orthogonal double-layer grating. The core of the segmentation algorithm is to construct a virtual single-layer grating after combining the velocities of the two layers of grating, and perform the slide-window segmentation of the single-layer grating. Finally, the conformal segments of the two layers of grating are used. This method provides a feasible scheme for sliding window segmentation of orthogonal double-layer grating.

In order to further reduce the segmentation error, the invention provides two optimization methods: blade motion trajectory optimization method and segment weight optimization method. The blade motion trajectory optimization method takes the trajectory of each blade as a variable and optimizes the objective function under certain constraints when the condition that the weight of segment is fixed. Segment weight optimization method is to optimize the time points of each segment when the blade motion trajectory is fixed. Both of the two optimization methods can reduce the error of the segmentation intensity and improve the optimization effect.

For the preferred method of implementation of the invention, it should be noted that, for ordinary technicians in the field, a number of transformations and improvements may be made without deviating from the creative conception of the invention, which are within the protection of the invention.

The invention claimed is:

1. A dynamic intensity-modulated segmentation method for an orthogonal double-layer grating device, comprising steps of:
   S1: constructing a virtual single-layer grating, velocity of the virtual single-layer grating being composed of velocity of orthogonal double-layer grating, and setting a blade thickness and a blade logarithm of the virtual single-layer grating;
   S2: obtaining an optimization intensity map, and then rotating the optimization intensity map according to an installation angle of the virtual single-layer grating obtained in Step S1;
   S3: carrying out dynamic intensity modulation calculation for the rotated optimization intensity map obtained in Step S2, results of the dynamic intensity modulation calculation including a time point of an inflection point of velocity and shapes of each segment, obtaining a preliminary calculated intensity map by stacking the shapes of each segment, and comparing the preliminary calculated intensity map with the optimization intensity map to check whether the segment formed by the virtual single-layer grating meets expectation;

S4: obtaining a real segment by inverse rotation of the segment formed by the virtual single-layer grating;

S5: using the orthogonal double-layer grating to conformal the inversely rotated segment obtained in step S4;

S6: checking whether the blades of the orthogonal double-layer grating are overspeed, and if overspeed, limiting the overspeed blades and allowing the blades to retreat.

2. The dynamic intensity-modulated segmentation method for the orthogonal double-layer grating device according to claim 1, wherein in step S1, the velocity of the virtual single-layer grating is velocity synthesis of orthogonal grating A and orthogonal grating B, and a magnitude and a direction of the velocity are v, θ calculated according to Equations (1) and (2) shown below, respectively;

$$v = \sqrt{v_1^2 + v_2^2} \quad (1)$$

$$\theta = \tan^{-1}\left(\frac{v_2}{v_1}\right) \quad (2)$$

Wherein, $v_1$ is a maximum velocity of a horizontal blade, and $v_2$ is a maximum velocity of a vertical blade, the blade thickness of the virtual single-layer grating is set as a smaller value, and the blade logarithm is set as a larger value, other attributes are consistent with the orthogonal grating A or the orthogonal grating B.

3. The dynamic intensity-modulated segmentation method for the orthogonal double-layer grating device according to claim 2, wherein in step S2, when the optimization intensity map is rotated according to the installation angle of the virtual single-layer grating obtained in step S1, a sampling interval of the optimization intensity map in the direction of the blade thickness is directly divided according to the blade thickness, and a sampling interval in the direction of the blade movement is divided according to a custom interval, with a value of 0.25.

4. The dynamic intensity-modulated segmentation method for the orthogonal double-layer grating device according to claim 3, wherein step S3 includes the following steps:

S3.1: calculating minimum increment of flux according to Equation 3;

in order to ensure that the blade will not be closed during movement, a minimum distance (Gap) between blade pairs is known, and when the blade runs unit length at a maximum physical speed, the flux per unit length is the minimum, and a product of minimum slope and Gap is the minimum intensity value that the blade can reach;

$$\min \text{slope} = \frac{DoseRatio}{MaxDose \times MaxSpeed} \quad (3)$$

S3.2: calculating the relationship between the flux and the distance, according to the optimization intensity map rotated in step S2 and the minimum increment of flux to determine a corresponding curve of intensity flux and a position during the movement of left and right blades;

S3.3: setting the inflection point of velocity, the inflection point of velocity being calculated according to a relationship curve between the flux and the distance;

S3.4: determining the position of the left and right blades in segments, taking the inflection point of velocity as the segmentation point, calculating the positions of the left and right blades at each segmentation point;

S3.5: checking blade acceleration, and if maximum acceleration of the blade exceeds a limit, reducing maximum velocity of the grating and repeating steps S3.1-S3.4;

S3.6: contrasting the intensity map, calculating the intensity map under the current segmentation and comparing the calculated intensity map with the optimization intensity map to determine an error, when the error is greater than a threshold, adjusting the intensity map under the current segmentation and repeating steps S3.1-S3.5.

5. The dynamic intensity-modulated segmentation method for the orthogonal double-layer grating according to claim 1, further comprising:

optimizing the time point of each segment under a condition of a fixed blade trajectory, an optimization function being calculated from two norms of a difference between the segmentation intensity map and the optimization intensity map, as shown in Equation (4);

$$J_{obj} = \|J_{opt} - J_{cal}\|_2 \quad (4)$$

wherein the segmentation intensity map is regarded as the linear superposition of each segment, as shown in Equation (5);

$$I_{cal} = \sum_u u_i I_{seg} \quad (5)$$

wherein, $I_{seg}$ is the intensity map formed by a single segment, $u_i$ is the weight of the segment, and the objective function is $J_{obj}$.

6. The dynamic intensity-modulated segmentation method for the orthogonal double-layer grating according to claim 1, further comprising:

optimizing an objective function under certain conditions by taking a motion trajectory of each blade as a variable under the condition that the weight of the segment is fixed.

7. The dynamic intensity-modulated segmentation method for the orthogonal double-layer grating blade according to claim 6, further comprising the following steps:

S7: calculating the intensity map formed by the superposition of the current blade position;

wherein the motion trajectory of each pair of blades of horizontal grating is denoted as:

$$X = \{x_{ly_1}(t), x_{ry_1}(t), x_{ly_2}(t), x_{ry_2}(t), \ldots, x_{ly_n}(t), x_{ry_n}(t)\} \quad (6)$$

the motion trajectory of each pair of blades of the vertical grating is denoted as:

$$Y = \{y_{dx_1}(t), y_{ux_1}(t), y_{dx_2}(t), y_{ux_2}(t), \ldots, y_{dx_m}(t), y_{ux_m}(t)\} \quad (7)$$

wherein, $x_{ly_i}(t)$ represents the motion trajectory of the left blade of the i-th pair of blades with a corresponding Y-axis coordinate being $y_i$; $x_{ry_i}(t)$ represents the motion trajectory of the right blade of the i-th pair of blades with the corresponding Y-axis coordinate being $y_i$; $y_{dx_j}(t)$ represents the motion trajectory of a lower blade of the j-th pair of blades with a corresponding X-axis coordinate being $x_j$; $y_{ux_j}(t)$ represents the motion trajectory of an upper blade of the j-th pair of blades the corresponding X-axis coordinate being $x_j$; there are n pairs of horizontal blades and m pairs of vertical blades;

blade movement is subject to constraints including jaw constraint, blade physical constraint and velocity constraint, the constraint conditions as shown in Equation (8)

$$\begin{cases} x_{min} \leq x_{ly_i}(t) \leq x_{ry_i}(t) \leq x_{max} \\ y_{min} \leq y_{dx_j}(t) \leq y_{ux_j}(t) \leq y_{max} \\ -v_{1max} \leq \dfrac{dx_{ly_i}(t)}{dt} \leq v_{1max}, -v_{1max} \leq \dfrac{dx_{ry_i}(t)}{dt} \leq v_{1max} \\ -v_{2max} \leq \dfrac{dy_{dx_j}(t)}{dt} \leq v_{2max}, -v_{2max} \leq \dfrac{dy_{ux_j}(t)}{dt} \leq v_{2max} \end{cases} \quad (8)$$

then, the calculated intensity map obtained from the above blade trajectory is calculated based on below Equations (9) and (10):

$$I(x, y) = \int_0^T H(x - x_{ly_i}(t)) \cdot H(x_{ry_i}(t) - x) \cdot H(y - y_{dx_j}(t)) \cdot H(y_{ux_j}(t) - y) \quad (9)$$

$$H(x) = \begin{cases} 1, x \geq 0 \\ 0, x < 0 \end{cases} \quad (10)$$

wherein, i and j are blade serial numbers of the horizontal grating and the vertical grating corresponding to the point (x, y);

the segmentation intensity map is regarded as a linear superposition of each segment, as shown in Equation (11);

$$I_{cal} = \sum_u u_i I_{seg} \quad (11)$$

wherein, $I_{seg}$ is the intensity map formed by a single segment, $u_i$ is the segment weight;

the objective function is $J_{obj}$, and an optimization objective function is calculated from two forms of a difference between the segmented intensity map and the optimization intensity map, as shown in Equation (12);

$$J_{obj} = \|J_{opt} - J_{cal}\|_2 \quad (12)$$

S8: starting an outer loop to find rows and columns that differ most from the segmentation intensity map and the optimization intensity map, an evaluation criterion of difference value being the two norms;

S9: finding a blade sequence number corresponding to the row and column with the greatest difference, when there is a fixed correspondence relationship between grating and intensity map, calculating the blade sequence number according to an intensity map number;

S10: starting an internal cycle, selecting a moment at random, calculating an activity range of four blades on the upper, lower, left and right sides according to the constraint conditions according to Equation (8);

S11: changing the position of the upper, lower, left and right blades in a cycle, according to step S10, the four blades being given a range of activity, the maximum and minimum values of the range of the four blades being taken in a cycle to perturb the positions of the four blades respectively;

S12: determining if the objective function has a decline or the internal cycle exceeds the limit, if the objecting function has the decline or the internal cycle exceeds the limit, performing step S13; otherwise, repeating step S10-S11;

S13: determining if the objective function is less than the threshold value or the external cycle exceeds the limit, if the objective function is less than the threshold value or the external cycle exceeds the limit, stopping the optimization, otherwise, repeating steps S8-S12.

\* \* \* \* \*